United States Patent
Ohishi et al.

(10) Patent No.: US 8,765,981 B2
(45) Date of Patent: Jul. 1, 2014

(54) PROCESS FOR PRODUCING OLEFIN OXIDE

(75) Inventors: Yoshihiko Ohishi, Osaka (JP); Anusorn Seubsai, Bangkok (TH); Selim Senkan, Los Angeles, CA (US)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/978,266

(22) PCT Filed: Dec. 15, 2011

(86) PCT No.: PCT/US2011/065142
§ 371 (c)(1),
(2), (4) Date: Jul. 3, 2013

(87) PCT Pub. No.: WO2012/094118
PCT Pub. Date: Jul. 12, 2012

(65) Prior Publication Data
US 2013/0281722 A1 Oct. 24, 2013

Related U.S. Application Data

(60) Provisional application No. 61/429,955, filed on Jan. 5, 2011.

(51) Int. Cl.
*C07D 301/03* (2006.01)
*B01J 27/13* (2006.01)
*B01J 21/00* (2006.01)
*B01J 23/72* (2006.01)
*B01J 23/58* (2006.01)

(52) U.S. Cl.
USPC ........... 549/536; 502/250; 502/331; 502/328; 549/523

(58) Field of Classification Search
USPC ........... 549/523, 536; 502/230, 250, 331, 328
See application file for complete search history.

(56) References Cited

U.S. PATENT DOCUMENTS

| | | |
|---|---|---|
| 4,826,802 A | 5/1989 | Sasaki et al. |
| 6,329,537 B1 | 12/2001 | Faraj |
| 6,500,969 B1 | 12/2002 | Zhou et al. |
| 6,765,101 B1 | 7/2004 | Bhasin et al. |
| 2001/0020105 A1 | 9/2001 | Hayashi et al. |
| 2003/0191328 A1 | 10/2003 | Jansen et al. |
| 2004/0068128 A1 | 4/2004 | Teles et al. |
| 2011/0152546 A1 | 6/2011 | Senkan et al. |
| 2011/0152547 A1 | 6/2011 | Senkan et al. |
| 2012/0283454 A1 | 11/2012 | Senkan et al. |
| 2012/0283455 A1 | 11/2012 | Senkan et al. |

FOREIGN PATENT DOCUMENTS

JP 2202-371074 A 12/2002

OTHER PUBLICATIONS

International Search Report for PCT/US2011/065142.

*Primary Examiner* — T. Victor Oh
(74) *Attorney, Agent, or Firm* — Sughrue Mion, PLLC

(57) ABSTRACT

A process for producing an olefin oxide which comprises reacting an olefin with oxygen in the presence of a catalyst comprising a copper oxide and a tellurium oxide.

19 Claims, No Drawings

PROCESS FOR PRODUCING OLEFIN OXIDE

CROSS REFERENCE TO RELATED APPLICATION

This is a National Stage Entry of Application No. PCT/US2011/065142 filed Dec. 15, 2011, claiming priority based on U.S. Provisional Application No. 61/429,955 filed Jan. 5, 2011, the contents of all of which are incorporated herein by reference in their entirety.

FIELD OF THE INVENTION

The present invention relates to a process for producing an olefin oxide.

BACKGROUND ART

As to a process for producing olefin oxides, olefin epoxidation in the presence of a metal-based catalyst has been proposed. For example, US2003/0191328 mentions a process for the epoxidation of hydrocarbon with oxygen in the presence of a mixture containing at least two metals from the specific metal group on a support having a specific BET surface area.

JP2002-371074 mentions a process for producing an oxirane compound which process uses a metal oxide catalyst containing at least one metal selected from the metals belonging to the Groups III to XVI of the periodic table.

SUMMARY OF THE INVENTION

The present invention provides:

[1] A process for producing an olefin oxide which comprises reacting an olefin with oxygen in the presence of a catalyst comprising a copper oxide and a tellurium component.

[2] The process according to [1], wherein the catalyst comprises a ruthenium oxide.

[3] The process according to [1] or [2], wherein the catalyst comprises an alkaline metal component or alkaline earth metal component.

[4] The process according to [1] or [2], wherein the catalyst comprises a halogen component.

[5] The process according to [1], wherein the copper oxide and the tellurium component are supported on a porous support.

[6] The process according to [2], wherein the copper oxide, the tellurium component and the ruthenium oxide are supported on a porous support.

[7] The process according to [3], wherein the copper oxide, the tellurium component, the ruthenium oxide and the alkaline metal component or alkaline earth metal component are supported on a porous support.

[8] The process according to [4], wherein the copper oxide, the tellurium component, the ruthenium oxide, the alkaline metal component or alkaline earth metal component and the halogen component are supported on a porous support.

[9] The process according to any one of [5] to [8] wherein the porous support comprises $Al_2O_3$, $SiO_2$, $TiO_2$ or $ZrO_2$.

[10] The process according to any one of [5] to [8], wherein the porous support comprises $SiO_2$.

[11] The process according to any one of [1] to [10], wherein the tellurium/copper molar ratio in the catalyst is 0.001/1 to 50/1.

[12] The process according to [2], wherein the ruthenium/copper molar ratio in the catalyst is 0.01/1 to 50/1.

[13] The process according to [3], wherein the alkaline or alkaline earth/copper molar ratio in the catalyst is 0.001/1 to 50/1.

[14] The process according to any one of [1] to [13], wherein the copper oxide is CuO.

[15] The process according to any one of [1] to [14], wherein the tellurium component comprises tellurium and an oxygen atom.

[16] The process according to [2], wherein the ruthenium oxide is $RuO_2$.

[17] The process according to [3], wherein the alkaline metal component or alkaline earth metal component is an alkaline metal-containing compound.

[18] The process according to [17], wherein the alkaline metal-containing compound is a sodium-containing compound or a potassium-containing compound.

[19] The process according to [5], wherein the total amount of the copper oxide and the tellurium component is 0.01 to 80 weight parts relative to 100 weight parts of a porous support.

[20] The process according to [5], wherein the catalyst is obtained by impregnating a porous support with a solution or a suspension containing a copper ion and a tellurium compound or ion, followed by calcining the composition obtained.

[21] The process according to [6], wherein the catalyst is obtained by impregnating a porous support with a solution or a suspension containing a copper ion, a tellurium compound or ion and a ruthenium ion to prepare a composition, followed by calcining the composition obtained.

[22] The process according to [7], wherein the catalyst is obtained by impregnating a porous support with a solution or a suspension containing a copper ion, a tellurium compound or ion, a ruthenium ion and an alkaline metal or alkaline earth metal ion to prepare a composition, followed by calcining the composition obtained.

[23] The process according to [8], wherein the catalyst is obtained by impregnating a porous support with a solution or a suspension containing a copper ion, a tellurium compound or ion, a ruthenium ion, an alkaline metal or alkaline earth metal ion and a halogen ion to prepare a composition, followed by calcining the composition obtained.

[24] The process according to any one of [1] to [23], wherein the olefin is propylene and the olefin oxide is propylene oxide.

[25] The process according to any one of [1] to [24], which comprises reacting an olefin with oxygen at a temperature of 100 to 350° C.

[26] A catalyst for production of an olefin oxide which comprises a copper oxide and a tellurium component.

[27] The catalyst according to [26], wherein the catalyst comprises a ruthenium oxide.

[28] The catalyst according to [26] or [27] which comprises an alkaline metal component or alkaline earth metal component.

[29] The catalyst according to any one of [26] to [28], which comprises a halogen component.

[30] The catalyst according to any one of [26] to [29], wherein the copper oxide is CuO.

[31] The catalyst according to any one of [26] to [30], wherein the tellurium component comprises tellurium and an oxygen atom.

[32] The catalyst according to any one of [27] to [31], wherein the ruthenium oxide is $RuO_2$.

[33] The catalyst according to any one of [28] to [32], wherein the alkaline metal component or alkaline earth metal component is an alkaline metal-containing compound.

[34] The catalyst according to [33], wherein the alkaline metal-containing compound is a sodium-containing compound or a potassium-containing compound.
[35] The catalyst according to [26], wherein the copper oxide and the tellurium component are supported on a porous support.
[36] The catalyst according to [27], wherein the copper oxide, the tellurium component and the ruthenium oxide are supported on a porous support.
[37] The catalyst according to [28], wherein the copper oxide, the tellurium component, the ruthenium oxide and the alkaline metal component or alkaline earth metal component are supported on a porous support.
[38] The catalyst according to [29], wherein the copper oxide, the tellurium component, the ruthenium oxide, the alkaline metal component or alkaline earth metal component and the halogen component are supported on a porous support.
[39] The catalyst according to any one of [35] to [38], wherein the porous support comprises $Al_2O_3$, $SiO_2$, $TiO_2$ or $ZrO_2$.
[40] The catalyst according to any one of [35] to [38], wherein the porous support comprises $SiO_2$.
[41] The catalyst according to any one of [26] to [40], wherein the tellurium/copper molar ratio in the catalyst is 0.001/1 to 50/1.
[42] The catalyst according to any one of [27] to [41], wherein the ruthenium/copper molar ratio in the catalyst is 0.01/1 to 50/1.
[43] The catalyst according to any one of [28] to [42], wherein the alkaline or alkaline earth metal/copper molar ratio in the catalyst is 0.001/1 to 50/1.
[44] The catalyst according to [35] which is obtained by impregnating a porous support with a solution or a suspension containing a copper ion and a tellurium compound or ion to prepare a composition, followed by calcining the composition obtained.
[45] The catalyst according to [36] which is obtained by impregnating a porous support with a solution or a suspension containing a copper ion, a tellurium compound or ion and a ruthenium ion to prepare a composition, followed by calcining the composition obtained.
[46] The catalyst according to [37], wherein the catalyst is obtained by impregnating a porous support with a solution or a suspension containing a copper ion, a tellurium compound or ion, a ruthenium ion and an alkaline metal or alkaline earth metal ion to prepare a composition, followed by calcining the composition obtained.
[47] The catalyst according to [38], wherein the catalyst is obtained by impregnating a porous support with a solution or a suspension containing a copper ion, a tellurium compound or ion, a ruthenium ion, an alkaline metal or alkaline earth metal ion and a halogen ion to prepare a composition, followed by calcining the composition obtained.
[48] The catalyst according to any one of [26] to [47], wherein the olefin oxide is propylene oxide.

DETAILED DESCRIPTION OF THE INVENTION

The process of the present invention comprises reacting an olefin with oxygen in the presence of a catalyst comprising (a) copper oxide and (b) tellurium component.
In the catalyst, the components (a) and (b) are preferably supported on a support, and more preferably on a porous support. This catalyst is valuable for production of olefin oxides, which is one aspect of the present invention.
The support may be a porous support, and may be a non-porous support.

The porous support has pores capable of supporting the components (a) and (b). The porous support comprises preferably $Al_2O_3$, $SiO_2$, $TiO_2$, or $ZrO_2$, more preferably $SiO_2$. Examples of the porous support comprising $SiO_2$ include mesoporous silica. Such a porous support may also comprise zeolites.
Examples of the non-porous support include a non-porous support comprising $SiO_2$ such as CAB-O-SIL (registered trademark).
The support may be in form of powder or may be shaped to a desired structure.
If the catalyst comprises $SiO_2$ as a support, olefin oxides can be prepared with good yield and good selectivity.
The catalyst may comprise one or more kinds of (a) copper oxide.
The (a) copper oxide is usually composed of copper and oxygen.
Examples of the copper oxide include $Cu_2O$ and $CuO$. The copper oxide is preferably $CuO$.
The catalyst may comprise one or more kinds of (b) tellurium component. The component (b) may be tellurium-containing compound or tellurium ion. Examples of the tellurium-containing compound include tellurium oxide such as TeO, $TeO_2$, $TeO_3$ or $Te_2O_5$, and tellurium salt with anion such as $Cl^-$, $Br^-$, $I^-$, $F^-$, $OH^-$, $NO^{3-}$ or $CO_3^{2-}$. Examples of the tellurium ion include $Te^{2+}$, $Te^{4+}$, $Te^{6+}$, $Te^{2-}$. The component (b) is preferably tellurium oxide, more preferably those comprising tellurium and an oxygen atom, still more preferably $TeO_2$.
The catalyst may comprise one or more kinds of (c) ruthenium oxide. The component (c) is usually composed of ruthenium and oxygen. Examples of the ruthenium oxide include $Ru_2O_4$, $Ru_2O_5$, $Ru_3O_5$, $Ru_3O_6$, $RuO_4$, and $RuO_2$. The component (c) is preferably $RuO_2$.
The catalyst may comprise one or more kinds of (d) alkaline metal component or alkaline earth metal component. In the catalyst, the component (d) may be supported on the above-mentioned porous support, or the components (a) and (b).
The component (d) may be an alkaline metal-containing compound, an alkaline earth metal-containing compound, an alkaline metal ion or an alkaline earth metal ion.
Examples of the alkaline metal-containing compound include compounds containing an alkaline metal such as Na, K, Rb and Cs. Examples of the alkaline earth metal-containing compound include compounds containing an alkaline earth metal such as Ca, Mg, Sr and Ba. Examples of the alkaline metal ion include $Na^+$, $K^+$, $Rb^+$ and $Cs^+$. Examples of the alkaline earth metal ion include such as $Ca^{2+}$, $Mg^{2+}$, $Sr^{2+}$ and $Ba^{2+}$.
The alkaline metal component may be an alkaline metal oxide. Examples of the alkaline metal oxide include $Na_2O$, $Na_2O_2$, $K_2O$, $K_2O_2$, $Rb_2O$, $Rb_2O_2$, $Cs_2O$, and $Cs_2O_2$. The alkaline earth metal component may be alkaline earth metal oxide. Examples of the alkaline earth metal oxide include CaO, CaO, MgO, $MgO_2$, SrO, $SrO_2$, BaO and $BaO_2$.
The component (d) is preferably an alkaline metal-containing compound, more preferably a sodium-containing compound or a potassium-containing compound, still more preferably a sodium-containing compound.
The alkaline metal-containing compound and alkaline earth metal-containing compound are preferably an alkaline metal salt and an alkaline earth metal salt. The alkaline metal salt comprises the alkaline metal ion as mentioned above with an anion. The alkaline earth metal salt comprises the alkaline earth metal ion as mentioned above with an anion. Examples of anions in such salts include $Cl^-$, $Br^-$, $I^-$, $F^-$, $OH^-$, $NO_3^-$, $SO_4^{2-}$ and $CO_3^{2-}$. Such salts are preferably an alkaline metal salt with a halogen, such as an alkaline metal halide, or an alkaline earth metal-containing salt with a halogen, such as an alkaline earth metal halide, more preferably an alkaline metal salt with a halogen, still more preferably an alkaline metal chloride.

The catalyst comprises preferably CuO and Te component, more preferably CuO, Te component and $RuO_2$, or CuO, Te component, $RuO_2$ and an alkaline metal-containing compound, still more preferably CuO, Te component, $RuO_2$ and a sodium-containing compound, because the olefin oxide yield and selectivity can be improved by adopting such combination to the production of an olefin oxide. Particularly if the catalyst comprises NaCl, as the (d) component, it can show excellent olefin oxide selectivity. Herein, the catalysts generally contain no silver element, which can be prepared without silver metal or silver-containing compounds.

The tellurium/copper molar ratio in the catalyst is preferably 0.001/1 to 50/1 based on their atoms. When the molar ratio falls within such a range, the olefin oxide yield and selectivity can be further improved. The lower limit of the molar ratio is more preferably 0.01/1, still more preferably 0.05/1. The upper limit of the molar ratio is more preferably 1/1, still more preferably 0.5/1.

The ruthenium/copper molar ratio in the catalyst is preferably 0.01/1 to 50/1 based on their atoms. When the molar ratio falls within such a range, the olefin oxide yield and selectivity can be further improved. The lower limit of the molar ratio is more preferably 0.1/1, still more preferably 0.15/1, and especially preferably 0.2/1. The upper limit of the molar ratio is more preferably 5/1, still more preferably 2/1, and especially preferably 1/1.

The (d) component/copper molar ratio in the catalyst is preferably 0.001/1 to 50/1 based on their atoms. When the molar ratio falls within such a range, the olefin oxide yield and selectivity can be further improved. The lower limit of the molar ratio is more preferably 0.01/1, still more preferably 0.1/1. The upper limit of the molar ratio is more preferably 10/1, still more preferably 5/1. The "(d) component" of the molar ratio represents the total molar ratio of the alkaline metal or alkaline earth metal existing in the (d) component and the alkaline metal or alkaline earth metal ion existing in the (d) component.

When the components (a) and (b), and optionally any of the components (c) and (d) are supported on a porous support in the catalyst, the total content of these components is preferably 0.01 to 80 weight parts relative to 100 weight parts of a porous support. When the total content falls within such a range, the olefin oxide yield and selectivity can be further improved. The lower limit of the total content is more preferably 0.05 weight parts, still more preferably 0.1 weight parts relative to 100 weight parts of a porous support. The upper limit of the total content is more preferably 50 weight parts, still more preferably 30 weight parts relative to 100 weight parts of a porous support.

The catalyst may comprise (e) halogen component besides the components (a), (b), (c) and (d). The component (e) is generally a halogen-containing compound. Examples of the halogen include chlorine, fluorine, iodine and bromine.

Examples of such a halogen-containing compound include copper halides such as CuCl and $CuCl_2$, tellurium halides such as $TeCl_2$ and $TeCl_4$, ruthenium halides such as $RuCl_3$ and copper oxyhalides such as $CuOCl_2$, $CuClO_4$, $ClO_2Cu(ClO_4)_3$ and $Cu_2O(ClO_4)_2$, tellurium oxyhalides such as $Te_6O_{11}Cl_{12}$, ruthenium oxyhalides such as $Ru_2OCl_4$, $Ru_2OCl_5$ and $Ru_2OCl_6$. If the catalyst comprises the component (e), the component may be supported on any of the components (a), (b) (c) and (d) or the porous support.

The catalyst may further comprise (f) composite oxides including those composed of copper, tellurium and oxygen, such as $CuTeO_4$, $CuTeO_3$ and $Cu_3TeO_6$, those composed of tellurium, sodium and oxygen, such as $Na_2TeO_3$, $Na_2TeO_4$, $Na_2Te_4O_9$, and $Na_4TeO_5$, and those composed of sodium, copper and oxygen, such as $NaCuO_2$, $Na_2CuO_2$, NaCuO and $Na_6Cu_2O_6$, those composed of ruthenium, tellurium and oxygen, those composed of ruthenium, copper and oxygen such as $RuCu_2O_2$, $RuCuClO_3$, $Ru_2CuO_6$, $Ru_2Cu_2O_2$, and those composed of ruthenium, sodium and oxygen.

If the catalyst comprises the component (f), the component may be supported on the porous support or any of the components (a), (b), (c), (d) and (e) as mentioned above.

When the catalyst contains ruthenium oxide, the molar ratio of V, Mo or W to ruthenium metal in the catalyst is preferably less than 0.25, and more preferably less than 0.1, and it is still more preferable that the catalyst substantially contains no V, Mo or W.

Production of the catalyst is not restricted to a specific process, and examples of which include the conventional methods such as an impregnation method, a precipitation method, a deposition precipitation method, a chemical vapour deposition method, a mechnano-chemical method, and a solid state reaction method, and an impregnation method is preferable.

When the components (a) and (b), optionally in addition with the component (c), (d), (e) or (f), are supported on a porous support in the catalyst, the catalyst can be obtained by impregnating a porous support with a solution or a suspension containing a copper ion, a tellurium compound or ion, and optionally a ruthenium ion, an alkaline metal or alkaline earth metal-containing ion and/or a halogen ion to prepare a composition, followed by calcining the composition.

The mixture obtained by impregnating the porous support with the solution or the suspension is preferably aged with stirring at a temperature of 5° C. to 100° C., and more preferably 10° C. to 50° C. The mixture can be used as it is, and is preferably aged for some time. Aging time is preferably in the range from 0.5 to 48 hours, and more preferably 1 to 25 hours.

The solution or suspension containing above-mentioned ions can be prepared by mixing a copper salt and a tellurium compound or salt, and optionally a ruthenium salt, an alkaline metal or alkaline earth metal-containing salt and/or a halogen-containing compound in a solvent. Examples of the copper salt include copper acetate, copper ammonium chloride, copper bromide, copper carbonate, copper ethoxide, copper hydroxide, copper iodide, copper isobutyrate, copper isopropoxide, copper oxalate, copper oxychroride, copper oxide, copper nitrates, and copper chlorides, and copper nitrates and copper chlorides are preferable.

Examples of the tellurium compound or salt include, a halide such as $TeF_6$, $TeBr_4$, $TeCl_4$ and $TeI_4$, an oxyhalide, oxide such as TeO, $TeO_2$ and $TeO_3$, an alkoxide such as $Te(OC_2H_5)_4$, a tellurate such as $H_2TeO_3$, $H_6TeO_6$, $Na_2TeO_3$ and $Na_2TeO_4$, preferably halide and oxide, more preferably oxide, still more preferably $TeO_2$.

Examples of the ruthenium salt include, a halide such as ruthenium bromide, ruthenium chloride, ruthenium iodide, an oxyhalide such as $Ru_2OCl_4$, $Ru_2OCl_5$ and $Ru_2OCl_6$, a halogeno complex such as $[RuCl_2(H_2O)_4]Cl$, an amine complex such as $[Ru(NH_3)_5H_2O]Cl_2$, $[Ru(NH_3)_5Cl]Cl_2$, $[Ru(NH_3)_6]Cl_2$ and $[Ru(NH_3)_6]Cl_3$, a carbonyl complex such as $Ru(CO)_5$ and $Ru_3(CO)_{12}$, a carboxylate complex such as $[Ru_3O(OCOCH_3)_6(H_2O)_3]$, ruthenium nitrosylchloride, and $[Ru_2(OCOR)_4]Cl$ (R=alkyl group having 1 to 3 carbon atoms), a nitrosyl complex such as [Ru (NH$_3$)$_5$ (NO)]Cl$_3$, [Ru (OH) (NH$_3$)$_4$ (NO)] (NO$_3$)$_2$ and [Ru (NO)] (NO$_3$)$_3$, an amine complex, an acetylacetonate complex, an oxide such as RuO$_2$, and ammonium salt such as (NH$_4$)$_2$RuCl$_6$, and ruthenium salt containing Cl is preferable.

The alkaline metal or alkaline earth metal salt for the solution may be the same as or different from the (d) component. Examples of the alkaline metal salt and the alkaline earth metal salt include alkaline metal nitrates, alkaline earth metal nitrates, alkaline metal halides, alkaline earth metal halides, alkaline metal acetates, alkaline earth metal acetates, alkaline metal butyrates, alkaline earth metal butyrates, alkaline metal benzoates, alkaline earth metal benzoates, alkaline metal alkoxides, alkaline earth metal alkoxides, alkaline metal carbonates, alkaline earth metal carbonates, alkaline metal citrates, alkaline earth metal citrates, alkaline metal formates, alkaline earth metal formates, alkaline metal hydrogen carbonates, alkaline earth metal hydrogen carbonates, alkaline metal hydroxides, alkaline earth metal hydroxides, alkaline metal hypochlorites, alkaline earth metal hypochlorites, alkaline metal halates, alkaline earth metal halates, alkaline metal nitrites, alkaline earth metal nitrites, alkaline metal oxalates, alkaline earth metal oxalates, alkaline metal perhalates, alkaline earth metal perhalates, alkaline metal propionates, alkaline earth metal propionates, alkaline metal tartrates and alkaline earth metal tartrates, and alkaline metal halides and alkaline metal nitrates are preferable, and NaNO$_3$ and NaCl are more preferable.

If an alkaline metal salt with a halogen or alkaline earth metal salt with a halogen is used for production of the catalyst, the catalyst comprising the components (a), (b), (c), (d) and (e) can be produced from a solution or a suspension obtained by mixing the copper salt, the tellurium salt and the alkaline metal salt or alkaline earth metal salt in a solvent. At least one of selected from the group consisting of the above-mentioned metal salts preferably contains a halogen ion, and more preferably a chloride ion. Such a halogen ion may form the (d) component such as NaCl and the (e) component such as halides and oxyhalides of Cu or Te. The solution may contain acidic or basic compounds in order to control its pH. Examples of the acid compounds include hydrochloric acid, nitric acid, nitrous acid, perchloric acid. Examples of basic compounds include alkaline metal hydroxides, amine compounds, imine compounds, hydrazine or hydrazine compounds, ammonia, hydroxylamine, hydroxyamine and ammonium hydroxides.

Examples of the solvent include water, alcohols such as methanol or ethanol, and ethers. The amount of the solvent is preferably 0.01 to 2000 parts by weight per part by weight of copper salt. If the catalyst contains the support, the amount of the solvent is preferably 0.01 to 500 parts by weight per part by weight of the support, and more preferably 0.1 to 100 parts by weight.

The composition as prepared by the impregnation is usually dried, and examples of the drying method include evaporation to dryness, spray drying, drum drying and flash drying. The composition as prepared by the impregnation is preferably dried at a temperature of 10° C. to 250° C., and more preferably 40° C. to 200° C., before calcining the composition. Drying may be performed under an atmosphere of air or also under an inert gas atmosphere (for example, Ar, N$_2$, He) at standard pressure or reduced pressure. A drying time is preferably in the range from 0.5 to 24 hours. After drying, the composition can be shaped to a desired structure as necessary.

Calcining the composition is not limited, but preferably may be performed under a gas atmosphere containing oxygen and/or inert gas such as nitrogen, helium and argon. Examples of such a gas include air, an oxygen gas, nitrous oxide, and other oxidizing gases. The gas may be used after being mixed at an appropriate ratio with a diluting gas such as nitrogen, helium, argon, and water vapor. An optimal temperature for calcination varies depending on the kind of the gas and the composition, however, a too high temperature may cause agglomeration of tellurium component and copper component. Accordingly, the calcination temperature is typically 250 to 800° C., preferably 400 to 600° C. The calcining time is preferably in the range from 0.5 hour to 24 hours.

The catalyst can be used as powder, but it is usual to shape it into desired structures such as spheres, pellets, cylinders, rings, hollow cylinders or stars. The catalyst can be shaped by a known procedure such as extrusion, ram extrusion, tableting. The calcination is normally performed after shaping into the desired structures, but it can also be performed before shaping them.

Next, the following explains a reaction of an olefin with oxygen in the presence of the catalyst as described above.

In the present invention, the olefin may have a linear or branched structure and contains usually 2 to 10, preferably 2 to 8 carbon atoms. The olefin may be a monoolefin or a diolefin. Examples of the monoolefin include ethylene, propylene, butene, pentene, hexene, heptene, octene, nonene, and decene. Examples of the diene include butadiene such as 1,3-butadiene or 1,2-butadiene. Examples of the olefin include preferably monoolefin, more preferably ethylene, propylene, butene, pentene, hexene, heptene and octene, still more preferably ethylene, propylene and butene, most preferably propylene.

The reaction is generally performed in the gas phase. In the reaction, the olefin and oxygen may be fed respectively in the form of a gas. Olefin and oxygen gases can be fed in the form of their mixed gas. Olefin and oxygen gases may be fed with diluent gases. Examples of diluent gases include nitrogen, methane, ethane, propane, carbon dioxide, or rare gases, such as argon and helium.

As the oxygen source, pure oxygen may be used, or a mixed gas containing a gas inactive to the reaction, such as air, may be used. The amount of oxygen used varies depending on the reaction type, the catalyst, the reaction temperature or the like. The amount of oxygen is typically 0.01 to 100 mol, and preferably 0.03 to 30 mol, and more preferably 0.05 to 10 mol, with respect to 1 mol of the olefin.

The reaction is performed at a temperature generally of 100 to 350° C., preferably of 120 to 330° C., more preferably of 170 to 310° C.

The reaction is usually carried out under reaction pressure in the range of reduced pressure to increased pressure. By carrying out the reaction under such a reaction pressure condition, the productivity and selectivity of olefin oxides can be improved. Reduced pressure means a pressure lower than atmospheric pressure. Increased pressure means a pressure higher than atmospheric pressure. The pressure is typically in the range of 0.01 to 3 MPa, and preferably in the range of 0.02 to 2 MPa, in the absolute pressure.

The gaseous hourly space velocity (Liters of gas at standard temperature and pressure passing over the one liter of packed catalyst per hour) is generally in the range of from 100 Nl/(l.h) to 100000 Nl/(l.h), preferably 500 Nl/(l.h) to 50000 Nl/(l.h). The linear velocity is generally in the range of from 0.0001 m/s to 500 m/s, and preferably in range of 0.001 m/s to 50 m/s.

The reaction may be carried out as a batch reaction or a continuous flow reaction, preferably as a continuous flow reaction for industrial application. The reaction of the present invention may be carried out by mixing an olefin and oxygen and then contacting the mixture with the catalyst under reduced pressure to the increased pressure.

The reactor type is not limited. Examples of the reactor type are fluid bed reactor, fixed bed reactor, moving bed reactor, and the like, preferably fixed bed reactor. In the case of using fixed bed reactor, single tube reactor or multi tube reactor can be employed. More than one reactor can be used. If the number of reactors is large, small reactors as for example microreactors, can be used, which can have multiple channels.

When a fixed bed reactor is used, the catalyst can be packed into the reactor or coated on the surface of the reactor wall. The coated type reactor is suitable for microreactors and the packed bed reactor is suitable for a large reactor.

Generally, the reaction mixture can be passed through the packed bed reactor in up-flow mode or in downflow mode.

Adiabatic type reactor or heat exchange type reactor may also be used. When adiabatic type reactor is used, a part of the reaction mixture from the reactor can be recycled into the reactor after heat-exchanging to control the reaction temperature.

When two or more reactors are used, the reactors can be arranged in series and/or in parallel. When two or more reactors arranged in series are used, a heat exchanger can be used between the reactors for controlling reaction temperature.

In the present invention, the olefin oxide may have a linear or branched structure and contains usually 2 to 10, preferably 2 to 8 carbon atoms. The olefin oxide may have one carbon-carbon double bond when the diolefin is applied for the reaction. Examples of the olefin oxide having one carbon-carbon double bond include 3,4-epoxy-1-butene. Examples of the olefin oxides include preferably ethylene oxide, propylene oxide, butene oxide, pentene oxide, hexene oxide, heptene oxide and octene oxide, more preferably ethylene oxide, propylene oxide and butene oxide, still more preferably propylene oxide.

The olefin oxide as obtained can be collected by absorption with a suitable solvent such as water and acetonitrile followed by conducting a method known in the art such as separation by distillation.

EXAMPLES

In Examples 1 to 7, each measurement was performed according to the following method:

A reaction gas was mixed with ethane (10 Nml/min) as an external standard, and then directly introduced in the TCD-GC equipped with a column of Gaskuropack 54 (2 m). All products in the reaction gas were collected for 1 hour with double methanol traps connected in series and cooled with an ice bath. The two methanol solutions were mixed together and added to anisole as an external standard, and then analyzed with two FID-GCs equipped with different columns, Pora-BOND U (25 m) and PoraBOND Q (25 m).

The detected products were propylene oxide (PO), acetone (AT), acetaldehyde (AD), $CO_x$ ($CO_2$ and CO), and propanal (PaL) and acrolein (AC).

Propylene conversions ($X_{PR}$) were determined from the following:

$$X_{PR} = \{[PO+AC+AT+PaL+CO_2/3]_{out}/[C_3H_6]_{in}\} \times 100\%;$$

and PO selectivities ($S_{PO}$) were then calculated using the following expression:

$$S_{PO} = \{[PO]/[PO+AC+AT+PaL+CO_2/3]\} \times 100\%$$

Each metal weight was determined from the amounts of the metal salts used for preparation of catalyst.

Example 1

A catalyst was prepared by a co-impregnation method. A predetermined weights (1.9 g) of an amorphous silica powder ($SiO_2$, Japan Aerosil, 380 $m^2$/g) was added to an aqueous solution mixture containing 0.30 g of $Cu(NO_3)_2$ (Wako), 0.04 g of $TeCl_4$(Wako), and 40 g of ion-exchanged water, followed by stirring it for 24 hours at room temperature in the air to impregnate the support with the metal salts. The resulting material was then heated at 100° C. until dried, and calcined at 500° C. for 12 hours in the air to give a catalyst.

The catalyst was evaluated by using a fixed-bed reactor. Filling a ½-inch reaction tube made of stainless steel with 1 mL of thus obtained catalyst, the reaction tube was supplied with 450 NmL/h of propylene, 900 NmL/h of the air, 990 NmL/h of a nitrogen gas to carry out the reaction at the reaction temperature of 200° C. and 250° C. under the condition of the increased pressure (equivalent to 0.3 MPa in the absolute pressure).

In the catalyst, the total amount of Cu and Te was 5.1 weight parts relative to 100 weight parts of $SiO_2$.

The results are shown in Table 1.

TABLE 1

| | | |
|---|---|---|
| Total metal loading (wt parts) | 5.1 | |
| Cu/Te (molar ratio of metal) | 1/0.1 | |
| Reaction temperature (° C.) | 200 | 250 |
| Propylene conversion (%) | 0.1 | 0.5 |
| Propylene oxide selectivity (%) | 6 | 6 |

Example 2

A catalyst was prepared by a co-impregnation method. A predetermined weights (1.9 g) of an amorphous silica powder ($SiO_2$, Japan Aerosil, 380 $m^2$/g) was added to an aqueous solution mixture containing 0.55 g of $(NH_4)_2RuCl_6$ (Aldrich), 0.30 g of $Cu(NO_3)_2$ (Wako), 0.04 g of $TeCl_4$(Wako), and 40 g of ion-exchanged water, followed by stirring it for 24 hours at room temperature in the air to impregnate the support with the metal salts. The resulting material was then heated at 100° C. until dried, and calcined at 500° C. for 12 hours in the air to give a catalyst.

In the catalyst, the total amount of Cu, Te and Ru was 13.3 weight parts relative to 100 weight parts of $SiO_2$.

The catalyst was evaluated in the same manners as Example 1. The results are shown in Table 2.

TABLE 2

| | | |
|---|---|---|
| Total metal loading (wt parts) | 13.3 | |
| Cu/Te/Ru (molar ratio of metal) | 1/0.1/1.3 | |
| Reaction temperature (° C.) | 200 | 250 |
| Propylene conversion (%) | 0.4 | 9.8 |
| Propylene oxide selectivity (%) | 33 | 5 |

Example 3

A catalyst was prepared by a co-impregnation method. A predetermined weights (1.9 g) of an amorphous silica powder ($SiO_2$, Japan Aerosil, 380 $m^2$/g) was added to an aqueous solution mixture containing 0.22 g of $(NH_4)_2RuCl_6$ (Aldrich), 0.30 g of Cu ($NO_3)_2$ (Wako), 0.04 g of $TeCl_4$(Wako), and 40 g of ion-exchanged water, followed by stirring it for 24 hours at room temperature in the air to impregnate the support with the metal salts. The resulting material was then heated at 100° C. until dried, and calcined at 500° C. for 12 hours in the air to give a catalyst.

In the catalyst, the total amount of Cu, Te and Ru was 10.4 weight parts relative to 100 weight parts of $SiO_2$.

The catalyst was evaluated in the same manners as Example 1. The results are shown in Table 3.

TABLE 3

| Total metal loading (wt parts) | 10.4 | |
|---|---|---|
| Cu/Te/Ru (molar ratio of metal) | 1/0.1/0.5 | |
| Reaction temperature (° C.) | 200 | 250 |
| Propylene conversion (%) | 0.3 | 2.3 |
| Propylene oxide selectivity (%) | 50 | 28 |

Example 4

A catalyst was prepared by a co-impregnation method. A predetermined weights (1.9 g) of an amorphous silica powder ($SiO_2$, Japan Aerosil, 380 m$^2$/g) was added to an aqueous solution mixture containing 0.30 g of Cu($NO_3$)$_2$ (Wako), 0.04 g of TeCl$_4$(Wako), 0.10 g of NaCl (Wako) and 40 g of ion-exchanged water, followed by stirring it for 24 hours at room temperature in the air to impregnate the support with the metal salts. The resulting material was then heated at 100° C. until dried, and calcined at 500° C. for 12 hours in the air to give a catalyst.

In the catalyst, the total amount of Cu, Te and Na was 7.1 weight parts relative to 100 weight parts of $SiO_2$.

The catalyst was evaluated in the same manners as Example 1. The results are shown in Table 4.

TABLE 4

| Total metal loading (wt parts) | 7.1 | |
|---|---|---|
| Cu/Te/Na (molar ratio of metal) | 1/0.1/1.4 | |
| Reaction temperature (° C.) | 200 | 250 |
| Propylene conversion (%) | 0.1 | 0.5 |
| Propylene oxide selectivity (%) | 31 | 25 |

Example 5

A catalyst was prepared by a co-impregnation method. A predetermined weights (1.9 g) of an amorphous silica powder ($SiO_2$, Japan Aerosil, 380 m$^2$/g) was added to an aqueous solution mixture containing 0.55 g of (NH$_4$)$_2$RuCl$_6$ (Aldrich), 0.30 g of Cu (NO$_3$)$_2$ (Wako), 0.04 g of TeCl$_4$ (Wako), 0.10 g of NaCl (Wako), and 40 g of ion-exchanged water, followed by stirring it for 24 hours at room temperature in the air to impregnate the support with the metal salts. The resulting material was then heated at 100° C. until dried, and calcined at 500° C. for 12 hours in the air to give a catalyst.

In the catalyst, the total amount of Cu, Te, Ru and Na was 15.3 weight parts relative to 100 weight parts of $SiO_2$.

The catalyst was evaluated in the same manners as Example 1. The results are shown in Table 5.

TABLE 5

| Total metal loading (wt parts) | 15.3 | |
|---|---|---|
| Cu/Te/Ru/Na (molar ratio of metal) | 1/0.1/1.3/1.4 | |
| Reaction temperature (° C.) | 200 | 250 |
| Propylene conversion (%) | 0.5 | 5.0 |
| Propylene oxide selectivity (%) | 47 | 26 |

The powder X-ray diffraction of the catalyst obtained in Example 5 was recorded on a Rigaku powder diffraction unit, RINT-2500V, with mono-chromatized Cu Kα radiation (λ=0.154 nm) at 40 kV and 300 mA. The diffraction pattern was identified by comparing with those included in the JCPDS database (Joint Committee of Powder Diffraction Standards). As a result, the peaks at 27.8°, 35.1° and 40.0° could be observed.

Example 6

A catalyst was prepared by a co-impregnation method. A predetermined weights (1.9 g) of an amorphous silica powder ($SiO_2$, Japan Aerosil, 380 m$^2$/g) was added to an aqueous solution mixture containing 0.22 g of (NH$_4$)$_2$RuCl$_6$ (Aldrich), 0.30 g of Cu(NO$_3$)$_2$ (Wako), 0.04 g of TeCl$_4$ (Wako), 0.10 g of NaCl (Wako), and 40 g of ion-exchanged water, followed by stirring it for 24 hours at room temperature in the air to impregnate the support with the metal salts. The resulting material was then heated at 100° C. until dried, and calcined at 500° C. for 12 hours in the air to give a catalyst.

In the catalyst, the total amount of Cu, Te, Ru and Na was 10.4 weight parts relative to 100 weight parts of $SiO_2$.

The catalyst was evaluated at 250° C. in the same manners as Example 1. The results are shown in Table 6.

TABLE 6

| Total metal loading (wt parts) | 10.4 |
|---|---|
| Cu/Te/Ru/Na (molar ratio of metal) | 1/0.1/0.5/1.4 |
| Reaction temperature (° C.) | 250 |
| Propylene conversion (%) | 4.0 |
| Propylene oxide selectivity (%) | 43 |

The powder X-ray diffraction of the catalyst obtained in Example 6 was carried out in the same condition as Example 5. As a result, the peaks at 27.8°, 35.1° and 40.0° could be observed.

Example 7

A catalyst was prepared by a co-impregnation method. A predetermined weights (1.9 g) of an amorphous silica powder ($SiO_2$, Japan Aerosil, 380 m$^2$/g) was added to an aqueous solution mixture containing 0.22 g of (NH$_4$)$_2$RuCl$_6$ (Aldrich), 0.30 g of Cu(NO$_3$)$_2$ (Wako), 0.03 g of TeO$_2$(Wako), 0.10 g of NaCl(Wako), and 40 g of ion-exchanged water, followed by stirring it for 24 hours at room temperature in the air to impregnate the support with the metal salts. The resulting material was then heated at 100° C. until dried, and calcined at 500° C. for 12 hours in the air to give a catalyst.

In the catalyst, the total amount of Cu, Te, Ru and Na was 10.4 weight parts relative to 100 weight parts of $SiO_2$. The catalyst was evaluated at 250° C. in the same manners as Example 1. The results are shown in Table 7.

TABLE 7

| Total metal loading (wt parts) | 10.4 |
|---|---|
| Cu/Te/Ru/Na (molar ratio of metal) | 1/0.1/0.5/1.4 |
| Reaction temperature (° C.) | 250 |
| Propylene conversion (%) | 4.3 |
| Propylene oxide selectivity (%) | 57 |

What we claim are:

1. A process for producing an olefin oxide which comprises reacting an olefin with oxygen in the presence of a catalyst comprising a copper oxide and a tellurium component in a gas phase, wherein the olefin and oxygen are fed in the form of gas, and the gaseous hourly space velocity, that is liters of gas at standard temperature and pressure passing over one liter of packed catalyst per hour, is in the range of from 100 Nl/(l.h) to 100,000 Nl/(l.h).

2. The process according to claim 1, wherein the catalyst comprises a ruthenium oxide.

3. The process according to claim 1, wherein the catalyst comprises an alkaline metal component or alkaline earth metal component.

4. The process according to claim 1, wherein the catalyst comprises a halogen component.

5. The process according to claim 1, wherein the copper oxide and the tellurium component are supported on a porous support.

6. The process according to claim 2, wherein the copper oxide, the tellurium component and the ruthenium oxide are supported on a porous support.

7. The process according to claim 3, where in the copper oxide, the tellurium component, the ruthenium oxide and the alkaline metal component or alkaline earth metal component are supported on a porous support.

8. The process according to claim 3, wherein the copper oxide, the tellurium component, the ruthenium oxide and the alkaline metal component or alkaline earth metal component, and the halogen component are supported on a porous support.

9. The process according to claim 5, wherein the porous support comprises $Al_2O_3$, $SiO_2$, $TiO_2$ or $ZrO_2$.

10. The process according to claim 5, wherein the porous support comprises $SiO_2$.

11. The process according to claim 1, wherein the tellurium/copper molar ratio in the catalyst is 0.001/1 to 50/1.

12. The process according to claim 2, wherein the ruthenium/copper molar ratio in the catalyst is 0.01/1 to 50/1.

13. The process according to claim 3, wherein the alkaline or alkaline earth/copper molar ratio in the catalyst is 0.001/1 to 50/1.

14. The process according to claim 1, wherein the copper oxide is CuO.

15. The process according to claim 1, wherein the tellurium component comprises tellurium and an oxygen atom.

16. The process according to claim 2, wherein the ruthenium oxide is $RuO_2$.

17. The process according to claim 1, wherein the linear velocity is in the range of from 0.0001 m/s to 500 m/s.

18. The process according to claim 1, wherein the reaction is performed in the range of 0.3 to 3 MPa.

19. The process according to claim 1, wherein the catalyst comprises a sodium-containing compound.

* * * * *